(12) United States Patent
Lebel et al.

(10) Patent No.: US 12,118,720 B2
(45) Date of Patent: Oct. 15, 2024

(54) SYSTEMS AND METHODS OF MAGNETIC RESONANCE IMAGE PROCESSING USING NEURAL NETWORKS HAVING REDUCED DIMENSIONALITY

(71) Applicant: GE PRECISION HEALTHCARE LLC, Wauwatosa, WI (US)

(72) Inventors: Robert Marc Lebel, Calgary (CA); Suryanarayanan S. Kaushik, Wauwatosa, WI (US); Graeme C. Mckinnon, Hartland, WI (US); Xucheng Zhu, Mountain View, CA (US)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 398 days.

(21) Appl. No.: 17/644,857

(22) Filed: Dec. 17, 2021

(65) Prior Publication Data

US 2023/0196556 A1    Jun. 22, 2023

(51) Int. Cl.
*G06T 7/00* (2017.01)
*G06N 3/04* (2023.01)
(Continued)

(52) U.S. Cl.
CPC .......... *G06T 7/0012* (2013.01); *G06N 3/045* (2023.01); *G06N 3/08* (2013.01); *G16H 30/40* (2018.01);
(Continued)

(58) Field of Classification Search
CPC ......... G06T 7/0012; G06T 2207/10088; G06T 2207/20081; G06T 2207/20084; G16H 30/40; G06N 3/045; G06N 3/08
See application file for complete search history.

(56) References Cited

U.S. PATENT DOCUMENTS

2021/0042998 A1*  2/2021  Samaniego ............. G06T 19/20
2022/0107378 A1*  4/2022  Dey ....................... G06N 3/084

OTHER PUBLICATIONS

Setio et al., "Pulmonary Nodule Detection in CT Images: False Positive Reduction Using Multi-View Convolutional Networks", in IEEE Transactions on Medical Imaging, vol. 35, No. 5, pp. 1160-1169, May 2016, doi: 10.1109/TMI.2016.2536809.

(Continued)

*Primary Examiner* — David F Dunphy
(74) *Attorney, Agent, or Firm* — Armstrong Teasdale LLP (57) ABSTRACT

A magnetic resonance (MR) image processing system is provided. The system includes an MR image processing computing device that includes at least one processor. The processor is programmed to execute a neural network model configured to receive crude MR data as an input and output processed MR images associated with the crude MR data, the crude MR data and the processed MR images having the first number of dimensions. The processor is also programmed to receive a pair of pristine data and corrupted data both having a second number of dimensions lower than the first number of dimensions. The corrupted data are the pristine data added with primitive features. The processor is further programmed to train the neural network model using the pair of the pristine data and the corrupted data. The trained neural network model is configured to change primitive features associated with the crude MR data.

19 Claims, 6 Drawing Sheets (51) Int. Cl.
　　　*G06N 3/045*　　　(2023.01)
　　　*G06N 3/08*　　　(2023.01)
　　　*G16H 30/40*　　　(2018.01)

(52) U.S. Cl.
　　　CPC ............... *G06T 2207/10088* (2013.01); *G06T 2207/20081* (2013.01); *G06T 2207/20084* (2013.01)

(56) References Cited

OTHER PUBLICATIONS

Su et al., "Multi-view Convolutional Neural Networks for 3D Shape Recognition", dated Sep. 27, 2015, Cornell University, arXiv:1505.00880, 12 pages, accessed online at URL: https://arxiv.org/abs/1505.00880.

Zha et al., "Deep Convolutional Neural Networks With Multiplane Consensus Labeling for Lung Function Quantification Using UTE Proton MRI", published Apr. 4, 2019, J. Magn. Reson. Imaging 2019; 50:1169-1181, DOI: 10.1002/jmri.26734.

\* cited by examiner

SYSTEMS AND METHODS OF MAGNETIC RESONANCE IMAGE PROCESSING USING NEURAL NETWORKS HAVING REDUCED DIMENSIONALITY

BACKGROUND

The field of the disclosure relates generally to systems and methods of image processing, and more particularly, to systems and methods of processing magnetic resonance (MR) images using a neural network model.

Magnetic resonance imaging (MRI) has proven useful in diagnosis of many diseases. MRI provides detailed images of soft tissues, abnormal tissues such as tumors, and other structures, which cannot be readily imaged by other imaging modalities, such as computed tomography (CT). Further, MRI operates without exposing patients to ionizing radiation experienced in modalities such as CT and x-rays.

A neural network model may be used to process MR images. Known systems and methods of STSs are disadvantaged in some aspects and improvements are desired.

BRIEF DESCRIPTION

In one aspect, a magnetic resonance (MR) image processing system is provided. The system includes an MR image processing computing device, the MR image processing computing device including at least one processor in communication with at least one memory device. The at least one processor is programmed to execute a neural network model, wherein the neural network model is configured to receive crude MR data having a first number of dimensions as an input and configured to output processed MR images associated with the crude MR data, the processed MR images having the first number of dimensions. The at least one processor is also programmed to receive a pair of pristine data and corrupted data, wherein the pristine data and the corrupted data have a second number of dimensions that is lower than the first number of dimensions, and the corrupted data are the pristine data added with primitive features. The at least one processor is further programmed to train the neural network model using the pair of the pristine data and the corrupted data by inputting the corrupted data to the neural network model, setting the pristine data as target outputs of the neural network model, analyzing the corrupted data using the neural network model, comparing outputs of the neural network model with the target outputs, and adjusting the neural network model based on the comparison. The trained neural network model is configured to change primitive features associated with the crude MR data.

In another aspect, an MR image processing system is provided. The system includes an MR image processing computing device, the MR image processing computing device including at least one processor in communication with at least one memory device. The at least one processor is programmed to receive crude MR data having a first number of dimensions. The at least one processor is also programmed to analyze the crude MR data using a neural network model, wherein the neural network model was trained with a pair of pristine data and corrupted data, the pristine data and the corrupted data having a second number of dimensions that is lower than the first number of dimensions. The corrupted data are the pristine data added with primitive features, and the neural network model is configured to take the crude MR data as input and output processed MR images of the crude MR data, the processed MR images having the first number of dimensions. The at least one processor is further programmed to derive the processed MR images of the crude MR data based on the analysis, and output the processed MR images.

DRAWINGS

Non-limiting and non-exhaustive embodiments are described with reference to the following Figures, wherein like reference numerals refer to like parts throughout the various drawings unless otherwise specified.

DETAILED DESCRIPTION

The disclosure includes systems and methods of processing magnetic resonance (MR) images of a subject using a neural network model. The neural network model has a lower dimension than the input MR data or output MR images. As used herein, a subject is a human, an animal, or a phantom. Images may be in 2D, 3D, or higher. MR data or images are described herein as an example for illustration purposes only. Systems and methods described herein may be applied to medical images acquired with other imaging modalities such as computed tomography (CT) or with a combined imaging modality of MR with other modalities such as MR-PET (positron emission tomography). Method aspects will be in part apparent and in part explicitly discussed in the following description.

A neural network model may be used to process MR data, such as image reconstruction or generation, image enhancement, or parameter mapping. Before the neural network model is used to analyze MR data, the neural network model needs to be trained. In MR, a neural network model is trained using two-dimensional (2D) image data, mainly for two reasons. Firstly, the computation and memory demand of training with data in three dimension (3D) or higher increases exponentially and places significant strain on computers, unlike the computation and memory demand of training with 2D data, which is manageable. As a result, training using data of 3D or higher may take a long time, such as a week or more.

Secondly, training data of 3D or higher are typically unavailable, especially medical images like MR images. Acquiring high-quality medical images of 3D or higher may not be physically feasible, especially for MR images. MRI is relatively slow compared to other image modalities such as CT or PET. To acquire MR images with high image quality or signal to noise ratio (SNR) may need to repeat the scanning. The increase of SNR is approximately square-root of the number of repetitions, instead of being proportional to the number of repetitions. After certain number of repetitions, the amount of increase in SNR achieved by increasing the number of repetitions is not apparent. On the other hand, the duration that a subject may be scanned is limited. An MRI scan typically lasts approximately one or two hours, which is uncomfortable or feasible for some patients. Accordingly, a desired SNR may not be achieved with reasonable increase of scan time. Moreover, to have a high temporal resolution and high spatial resolution of 3D perfusion images may not be feasible in dynamic MR images such as MR perfusion images. Dynamic MR images are a series of MR images acquired over a period of time and used to study a dynamic response such as perfusion or metabolism of a subject. There is a trade-off between temporal and spatial resolutions in dynamic imaging. Acquiring a 3D volume takes much longer than 2D images, and therefore 3D dynamic images do not have the same level of temporal resolution of 2D dynamic images of the same spatial resolutions. In addition, because acquiring a 3D volume takes longer than a 2D slice, 3D images are relatively more susceptible to distortion caused by motion than 2D images, further increasing the difficulties in procuring high quality training data of 3D or higher.

Systems and methods described herein address the above long-felt need by using a neural network model that includes neural networks having a lower dimension than the input and output data and is trained with data having the lower dimension.

In known systems that use lower dimension neural networks to process higher dimension inputs, higher dimension inputs are preprocessed into data of the lower dimension before being input into the neural networks and the outputs of the neural networks are postprocessed back into the higher dimension. For example, to segment 3D images, the 3D images are transformed into stacks of the 2D images along various orientations, and the stacks 2D images are input into 2D neural networks. The 2D neural networks output segmented 2D images. The 2D segment images are morphed or rendered into 3D images. The training of the networks require the training data having the higher dimension.

In contrast, in the systems and methods described herein, higher dimension data are input into a lower dimension neural network model and outputs of the neural network model are in the higher dimension. In the meantime. The neural network model is trained with lower dimensional training data, and does not need to be trained with higher dimension training data.

In known methods, 2D networks are used to reconstruct undersampled 3D data by only applying the neural network along the undersampled dimensions. For example, a typical 3D scan fully samples the kx dimension while undersampling along ky and kz. A 2D reconstruction network is applied along ky and kz while treating kx as an independent dimension.

In contrast, in the systems and methods described here, neural network model is applied along multiple combinations of dimensions. For example, lower-dimension neural networks of the neural network model may be applied along multiple combination of kx/x, ky/x, and kz/z dimensions. As a result, the confidence level of inference by the neural network model is increased.

In magnetic resonance imaging (MRI), a subject is placed in a magnet. When the subject is in the magnetic field generated by the magnet, magnetic moments of nuclei, such as protons, attempt to align with the magnetic field but precess about the magnetic field in a random order at the nuclei's Larmor frequency. The magnetic field of the magnet is referred to as B0 and extends in the longitudinal or z direction. In acquiring an MRI image, a magnetic field (referred to as an excitation field B1), which is in the x-y plane and near the Larmor frequency, is generated by a radio-frequency (RF) coil and may be used to rotate, or "tip," the net magnetic moment Mz of the nuclei from the z direction to the transverse or x-y plane. A signal, which is referred to as an MR signal, is emitted by the nuclei, after the excitation signal B1 is terminated. To use the MR signals to generate an image of a subject, magnetic field gradient pulses (Gx, Gy, and Gz) are used. The gradient pulses are used to scan through the k-space, the space of spatial frequencies or inverse of distances. A Fourier relationship exists between the acquired MR signals and an image of the subject, and therefore the image of the subject can be derived by reconstructing the MR signals.

Figure 1:
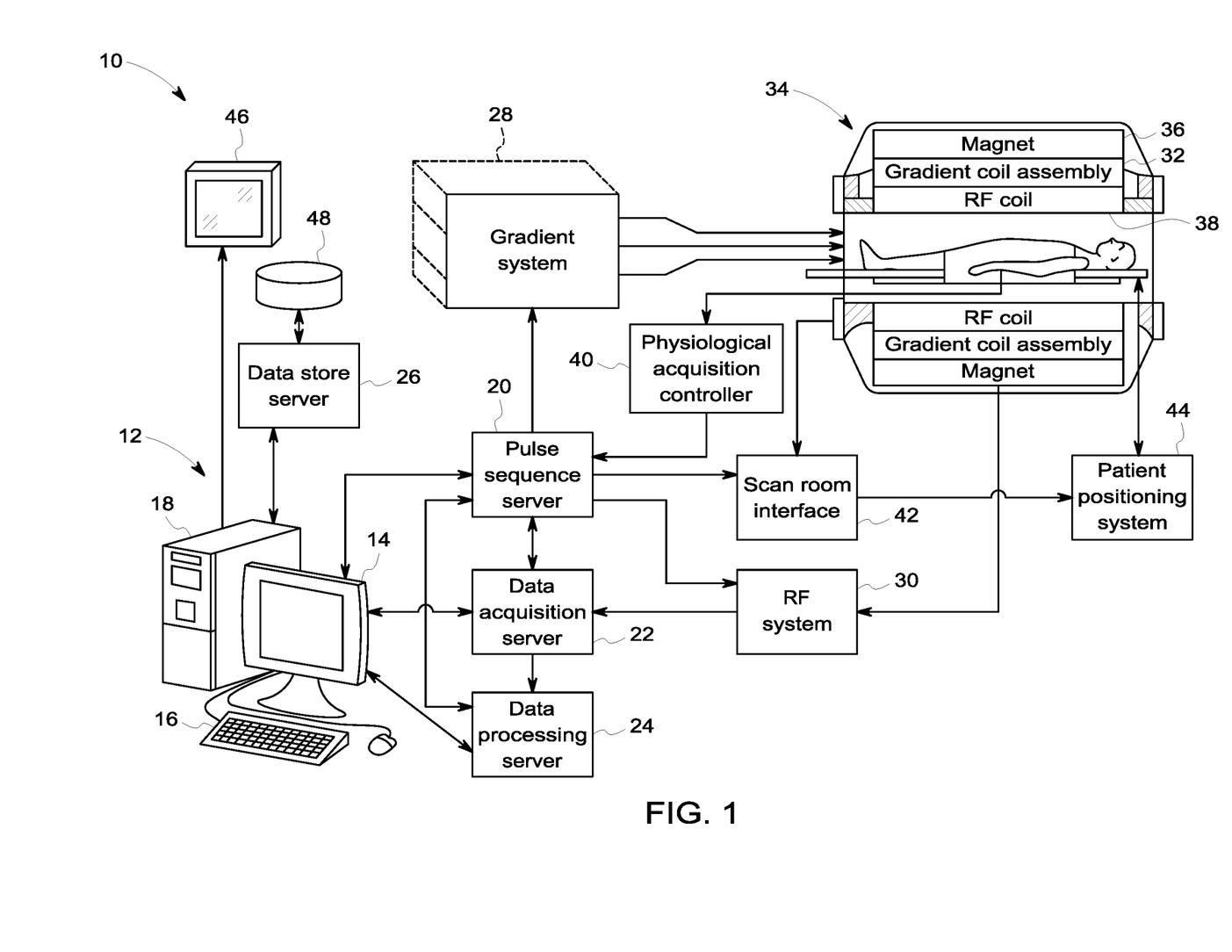
FIG. 1 is a schematic diagram of an exemplary magnetic resonance imaging (MRI) system.

FIG. 1 illustrates a schematic diagram of an exemplary MRI system 10. In the exemplary embodiment, MRI system 10 includes a workstation 12 having a display 14 and a keyboard 16. Workstation 12 includes a processor 18, such as a commercially available programmable machine running a commercially available operating system. Workstation 12 provides an operator interface that allows scan prescriptions to be entered into MRI system 10. Workstation 12 is coupled to a pulse sequence server 20, a data acquisition server 22, a data processing server 24, and a data store server 26. Workstation 12 and each server 20, 22, 24, and 26 communicate with each other.

In the exemplary embodiment, pulse sequence server 20 responds to instructions downloaded from workstation 12 to operate a gradient system 28 and a radiofrequency ("RF") system 30. The instructions are used to produce gradient and RF waveforms in MR pulse sequences. An RF coil 38 and a gradient coil assembly 32 are used to perform the prescribed MR pulse sequence. RF coil 38 is shown as a whole body RF coil. RF coil 38 may also be a local coil that may be placed in proximity to the anatomy to be imaged, or a coil array that includes a plurality of coils.

In the exemplary embodiment, gradient waveforms used to perform the prescribed scan are produced and applied to gradient system 28, which excites gradient coils in gradient coil assembly 32 to produce the magnetic field gradients $G_x$, $G_y$, and $G_z$ used for position-encoding MR signals. Gradient coil assembly 32 forms part of a magnet assembly 34 that also includes a polarizing magnet 36 and RF coil 38.

In the exemplary embodiment, RF system 30 includes an RF transmitter for producing RF pulses used in MR pulse sequences. The RF transmitter is responsive to the scan prescription and direction from pulse sequence server 20 to produce RF pulses of a desired frequency, phase, and pulse amplitude waveform. The generated RF pulses may be applied to RF coil 38 by RF system 30. Responsive MR signals detected by RF coil 38 are received by RF system 30, amplified, demodulated, filtered, and digitized under direction of commands produced by pulse sequence server 20. RF coil 38 is described as a transmitter and receiver coil such that RF coil 38 transmits RF pulses and detects MR signals. In one embodiment, MRI system 10 may include a transmitter RF coil that transmits RF pulses and a separate receiver coil that detects MR signals. A transmission channel of RF system 30 may be connected to a RF transmission coil and a receiver channel may be connected to a separate RF receiver coil. Often, the transmission channel is connected to the whole body RF coil 38 and each receiver section is connected to a separate local RF coil.

In the exemplary embodiment, RF system 30 also includes one or more RF receiver channels. Each RF receiver channel includes an RF amplifier that amplifies the MR signal received by RF coil 38 to which the channel is connected, and a detector that detects and digitizes the I and Q quadrature components of the received MR signal. The magnitude of the received MR signal may then be determined as the square root of the sum of the squares of the I and Q components as in Eq. (1) below:

$$M=\sqrt{I^2+Q^2} \quad (1);$$

and the phase of the received MR signal may also be determined as in Eq. (2) below:

$$\varphi = \tan^{-1}\left(\frac{Q}{I}\right). \quad (2)$$

In the exemplary embodiment, the digitized MR signal samples produced by RF system 30 are received by data acquisition server 22. Data acquisition server 22 may operate in response to instructions downloaded from workstation 12 to receive real-time MR data and provide buffer storage such that no data is lost by data overrun. In some scans, data acquisition server 22 does little more than pass the acquired MR data to data processing server 24. In scans that need information derived from acquired MR data to control further performance of the scan, however, data acquisition server 22 is programmed to produce the needed information and convey it to pulse sequence server 20. For example, during prescans, MR data is acquired and used to calibrate the pulse sequence performed by pulse sequence server 20. Also, navigator signals may be acquired during a scan and used to adjust the operating parameters of RF system 30 or gradient system 28, or to control the view order in which k-space is sampled.

In the exemplary embodiment, data processing server 24 receives MR data from data acquisition server 22 and processes it in accordance with instructions downloaded from workstation 12. Such processing may include, for example, Fourier transformation of raw k-space MR data to produce two or three-dimensional images, the application of filters to a reconstructed image, the performance of a back-projection image reconstruction of acquired MR data, the generation of functional MR images, and the calculation of motion or flow images.

In the exemplary embodiment, images reconstructed by data processing server 24 are conveyed back to, and stored at, workstation 12. In some embodiments, real-time images are stored in a database memory cache (not shown in FIG. 1), from which they may be output to operator display 14 or a display 46 that is located near magnet assembly 34 for use by attending physicians. Batch mode images or selected real time images may be stored in a host database on disc storage 48 or on a cloud. When such images have been reconstructed and transferred to storage, data processing server 24 notifies data store server 26. workstation 12 may be used by an operator to archive the images, produce films, or send the images via a network to other facilities.

Figure 2A:
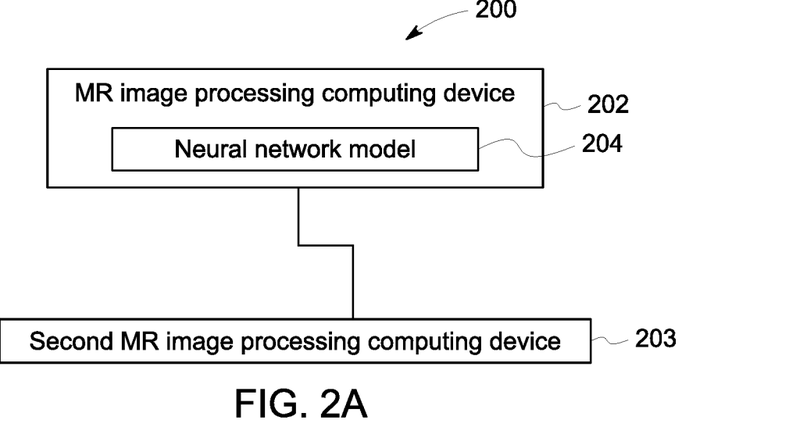
FIG. 2A is an exemplary MR image processing system.

FIG. 2A is a schematic diagram of an exemplary MR image processing system 200. In the exemplary embodiment, the system 200 includes a MR image processing computing device 202 configured to process MR data. As used herein, MR data may be MR k-space data, MR images, or data in a hybrid space where some dimension(s) are in k-space and other dimension(s) are in real space. The computing device 202 further includes a neural network model 204. The system 200 may include a second MR image processing computing device 203. Second MR image processing computing device 203 may be used to train the neural network model 204, and MR image processing computing device 202 may then use trained neural network model 204. Second MR image processing computing device 203 may be the same computing device as MR image processing computing device 202 such that the training and use of neural network model 204 are on one computing device. Alternatively, second MR image processing computing device 203 may be a computing device separate from MR image processing computing device 202 such that the training and use of neural network model 204 are executed on separate computing devices. MR image processing computing device 202 may be included in workstation 12 of MRI system 10, or may be included on a separate computing device that is in communication with workstation 12.

Figure 2B:
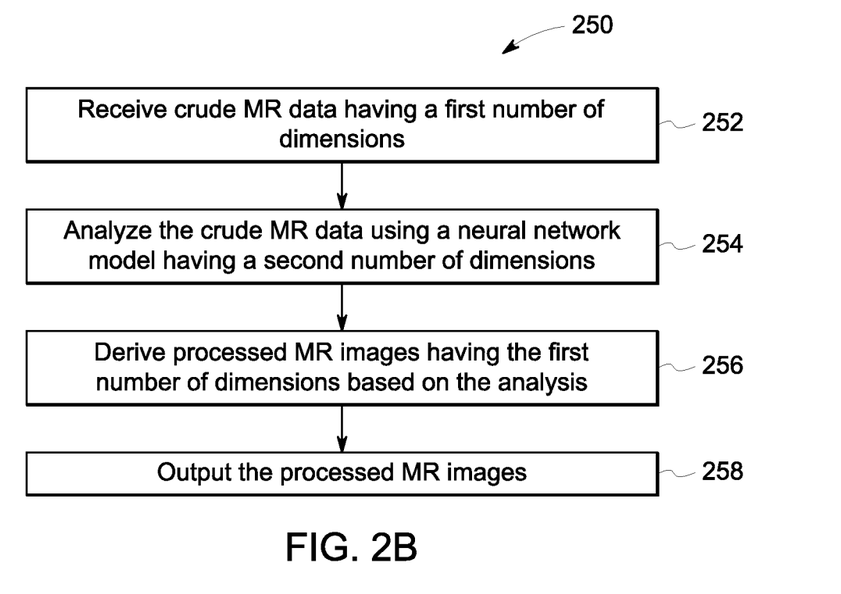
FIG. 2B is a flow chart of an exemplary method of image processing.

FIG. 2B is a flow chart of an exemplary method 250. Method 250 may be implemented on MR image processing system 200. In the exemplary embodiment, method 250 includes executing a neural network model, where the neural network model is deployed for analyzing data and the neural network model may have or have not been trained. Method 250 includes receiving 252 crude MR data having first number of dimensions. Method 250 includes analyzing 254 the crude MR data using a neural network model. Neural network model 204 has a second number of dimensions that is lower than the first number of dimensions. Neural network model 204 is trained with training data having the second number of dimensions. Method 250 further includes deriving 256 processed MR images of the crude MR data based on the analysis. Method 250 also includes outputting 258 the processed MR images.

In the exemplary embodiment, input crude MR data 302 have a first number of dimensions and output processed MR images 304 have the first number of dimensions (see FIGS. 3 and 4 described later). For example, crude MR data 302 and processed MR images 304 are both in 3D. Crude MR data 302 are MR k-space data of a 3D volume, MR images of a 3D volume, or MR data of a 3D volume in a hybrid space such as one or two dimensions being in k-space and the other dimension(s) in real space. The range of data in k-space tends to be much larger than the range of the data in real space because the center of the k-space has a much great signal than the peripheral of the k-space. The correlation of data may be more evident in the real space than in the k-space. Therefore, for example, the read-out dimension of crude MR data 302 may be in real space while phase-encoding dimension may be in k-space. Crude MR data 302 in a hybrid space may be used for parallel image reconstruction, which is reconstruction of images acquired with multiple RF coils or channels. MR data may be in 4D, such as dynamic MR data, which are MR data acquired along a period of time. The fourth dimension of dynamic MR data may be time or temporal frequency. MR data may be in 5D or higher.

Crude MR data 302 may be MR images that need to be enhanced. For example, crude MR data 302 may have a relatively high level of noise, artifacts like ringing and streaking, or distortion or artifacts from motion. Processed MR images are images with reduced noise, artifacts, or distortion. In some embodiments, neural network model 204 is configured to synthesize missing data points or reconstruct images. For example, crude MR data are data acquired by undersampling in one or more dimensions of kx, ky, or kz, e.g., partial-sampling the k-space in one of the k-space dimensions. Neural network model 204 is configured to generate data in the missing data and output processed MR images that are fully-sampled along the undersampled dimension. In other embodiments, neural network model 204 is configured to generate parameter maps of crude MR data 302. Processed MR images 304 are maps of parameters such as T1, or conversion of crude MR data 302 from MR images to pseudo CT images, which mimic the contrast of images acquired by another image modality such as CT or PET.

In the exemplary embodiment, neural network model 204 has a second number of dimensions and is trained with training data having a second number of dimensions. For example, neural network model 204 includes 2D neural networks and is trained with 2D images. Training neural network model 204 with 2D data takes less time and place less strain on computation and memory, compared to training with 3D data. The training data may be pairs of pristine data and corrupted data. Corrupted data may be produced based on pristine data such as adding primitive features to the pristine data. Primitive features may be noise, artifacts, or distortion. Unlike signals, which represent the anatomies or structures of the subject, artifacts are visual anomalies in the medical images that are not present in the subject, which may be caused by the imaging modality such as partial sampling pulse sequences. Primitive features may be contrast or edges common to a type of MR imaging or an MR parameter such as T1. Pristine data are data without the primitive features. Pristine data may nonmedical images or medical images. Pristine data may be non-MR data, such as natural images, synthetic images, or other nonmedical images or images or data acquired with an imaging modality other than MR. Pristine data may be k-space data or data in a hybrid space. Neural network model 204 is not content specific or is content independent, where performance of neural network model 204 is substantially unaffected by the content of the images. Instead, neural network model 204 is configured to detect primitive features in MR data associated with certain scanning, sampling, or data acquisition in MR, such as noise, artifacts, contrast, or patterns. Neural network model 204 is configured to use the primitive features to enhance, reconstruct, or convert crude MR data, such as to remove or reduce noise, artifacts, or distortion, or to convert crude MR data to pseudo-CT images. Because neural network model 204 is not content specific, neural network model 204 trained with training data having a lower number of dimensions may be used to detect the primitive features and process crude MR data having a higher number of dimensions and output processed images having the higher number of dimensions with primitive features changed. Neural network model 204 does not need to be trained with training data having the higher number of dimensions.

Figure 3:
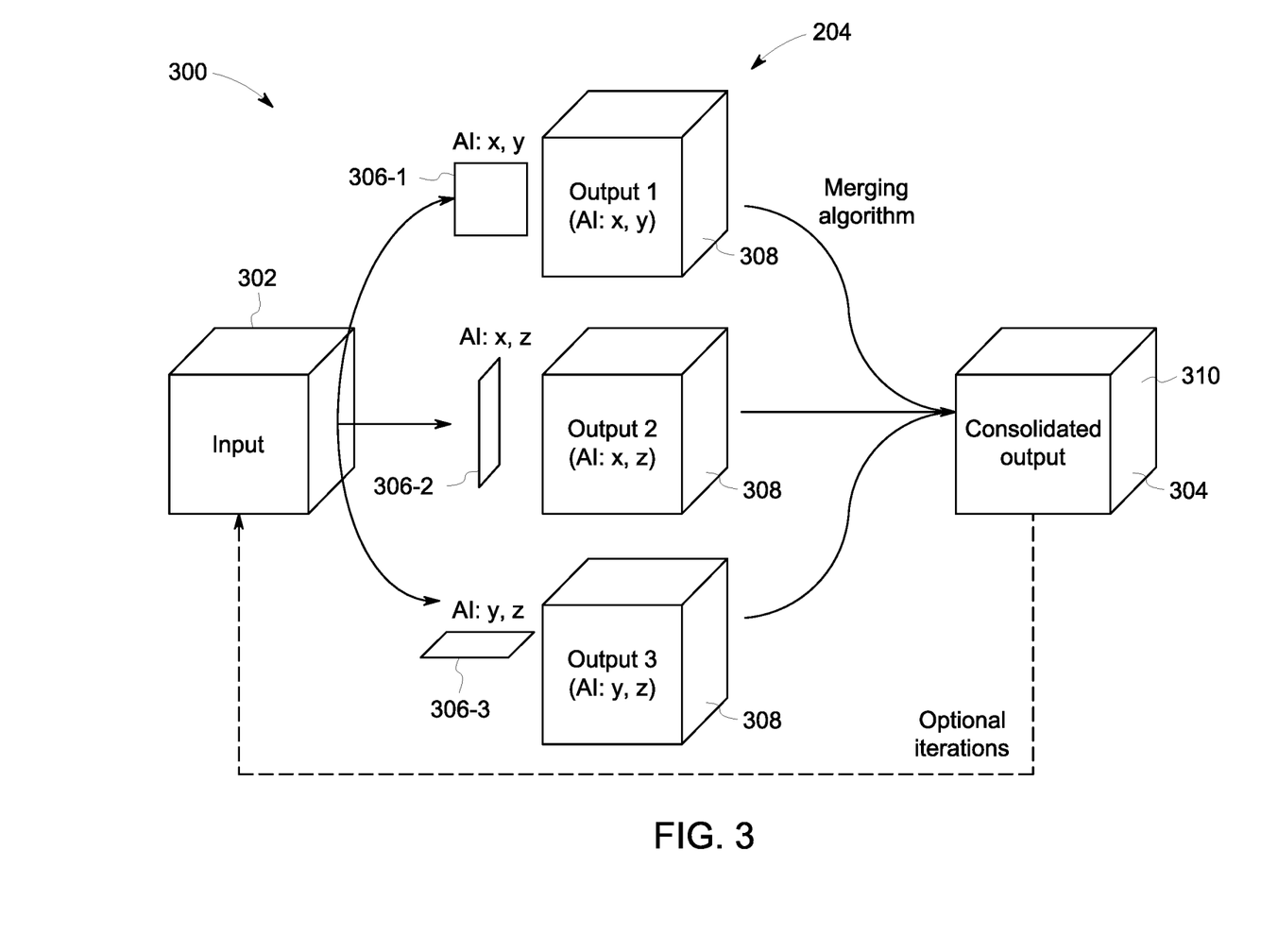
FIG. 3 is a process flow of an exemplary neural network model for the system shown in FIG. 2A.
Figure 4:
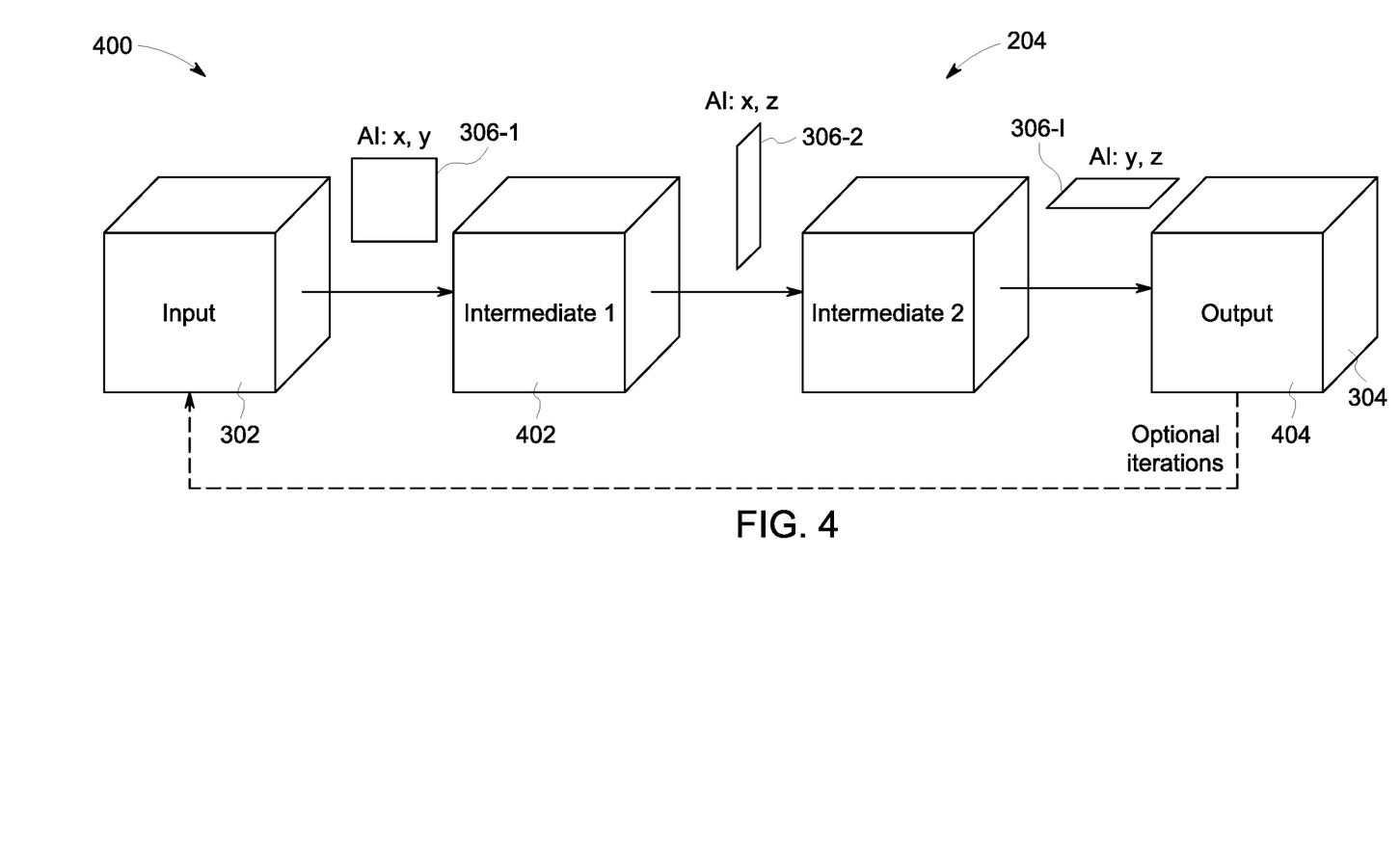
FIG. 4 is a process flow of another exemplary neural network model for the system shown in FIG. 2A.

In the exemplary embodiment, neural network model 204 may include a plurality of neural networks 306 (FIGS. 3 and 4 described later). Neural network 306 has a lower number of dimensions than crude MR data 302 and processed MR images 304. To increase confidence level of inference by neural network model 204, each dimension in crude MR data is analyzed at least twice by different neural networks 306. For example, the x/kx dimension is processed by neural network 306-1, 306-3.

In the exemplary embodiment, neural networks 306 may be iteratively applied to refine solution or increase the confidence level of the inference. For example, neural networks 306 are applied a number of times until a stable prediction is reached. In some embodiments, one or more of neural networks 306 are applied iteratively, while other neural networks are applied once. For example, if crude MR data 302 are acquired by undersampling in k-space in one dimension kx. Neural networks 306 that include the kx dimension is iteratively applied while neural networks that do not include the kx dimension is not iteratively applied.

FIG. 3 is a schematic diagram of an exemplary process flow 300 in an exemplary embodiment of neural network model 204. In the exemplary embodiment, neural network model 204 includes three 2D neural networks 306-1, 306-2, 306-3. Neural networks 306 are applied in parallel on crude MR data 302. Neural networks 306-1, 306-2, 306-3 are independent from one another. Each of neural network 306 operate on a different combination of input dimensions. For example, neural network 306-1 operate on crude MR data 302 along dimensions of x/kx and y/ky, neural network 306-2 operate on crude MR data 302 along dimensions of x/kx and z/kz, and neutral network 306-3 operate on crude MR data 302 along dimension of y/ky and z/kz. Neural networks 306-1, 306-2, 306-3 may be the same or different neural network. In some embodiments, one or more of neural networks 306-1, 306-2, 306-3 are trained differently from others. For example, in undersampling, kx is undersampled differently from ky or kz. kx may be undersampled by acquiring a kx line with a fractional echo by changing the echo time during scanning. On the other hand, ky or kz may be undersampled by reducing the number of ky or kz encoding. The associated training data are different because of the different undersampling patterns. In other embodiments, one or more neural networks 306-1, 306-2, 306-3 are different neural networks. For example, a receptive field, the portion of pixels across the images that a network sees or receives inputs from, may be larger in the undersmapled dimension(s) than fully-sample dimension(s). In another example, if one of the dimension is time/temporal frequency and the data is in a cine pattern, the neural network 306 having the time/temporal frequency dimension may include cyclic symmetry. 2D neural networks 306 are used as an example only. Neural networks 306 may be neural networks in other lower dimension or in combination of different lower dimensions. For example, neural networks 306 are 1D or a combination of 1D and 2D neural networks. Neural networks 306 may be different types of neural network. For example, neural network 306 may be convolutional network(s) in one or more dimensions while other dimension(s) are densely connected networks.

In the exemplary embodiment, each of neural networks 306 provides an output 308 having the same dimension as crude MR data 302. Outputs 308 are consolidated using a merging algorithm, such as the final output 310 of neural network model 204 or processed MR images 304 being an average or a weighted sum of outputs 308 of individual neural networks 306. Alternatively, outputs are consolidated through an agent, which is an entity in a machine learning model that applies a change to parameters of the machine learning model using a reward function based on a comparison between predictions by the model and ground truth/actual data. For example, during training, the agent may adjust the parameters in the consolidation of outputs 308 based on the comparison between the pristine data and corrupted data.

FIG. 4 is a schematic diagram of a process flow 400 of another exemplary embodiment of neural network model 204. Different from neural network model 204 shown in FIG. 3, neural networks 306 shown in FIG. 4 are applied sequentially or in series. In the exemplary embodiment, crude MR data 302 is input into 306-1, an output 402 of 306-1 is input into the next neural network 306, and an output 404 of the last neural network 306-1 is the output or processed MR images 304 of neural network model 204. For example, in image denoising or enhancement, noise, artifacts, or undersampling may be along one or two dimensions. Neural network 306 having those dimensions may be applied first to improve images along those dimensions before applying neural networks having only other dimension(s).

Figure 5A:
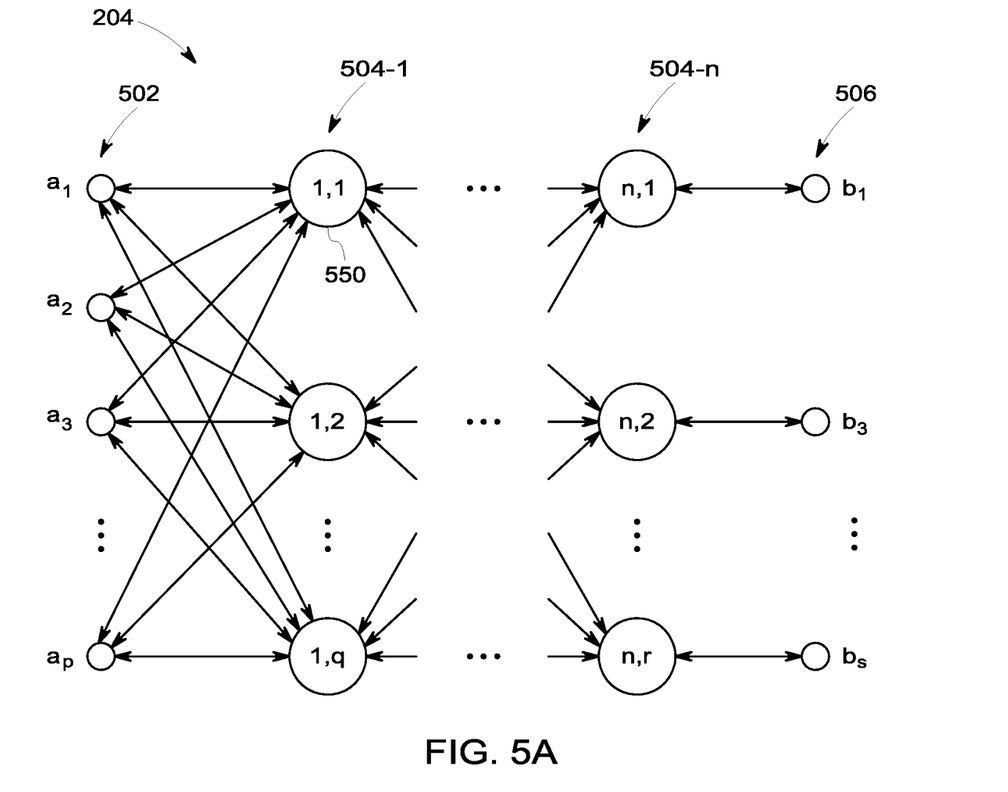
FIG. 5A is a schematic diagram of a neural network model.

FIG. 5A depicts an exemplary artificial neural network model 204. The exemplary neural network model 204 includes layers of neurons 502, 504-1 to 504-$n$, and 506, including an input layer 502, one or more hidden layers 504-1 through 504-$n$, and an output layer 506. Each layer may include any number of neurons, i.e., q, r, and n in FIG. 5A may be any positive integers. It should be understood that neural networks of a different structure and configuration from that depicted in FIG. 8A may be used to achieve the methods and systems described herein.

In the exemplary embodiment, the input layer 502 may receive different input data. For example, the input layer 502 includes a first input $a_1$ representing training images, a second input $a_2$ representing patterns identified in the training images, a third input $a_3$ representing edges of the training images, and so on. The input layer 502 may include thousands or more inputs. In some embodiments, the number of elements used by the neural network model 204 changes during the training process, and some neurons are bypassed or ignored if, for example, during execution of the neural network, they are determined to be of less relevance.

In the exemplary embodiment, each neuron in hidden layer(s) 504-1 through 504-$n$ processes one or more inputs from the input layer 502, and/or one or more outputs from neurons in one of the previous hidden layers, to generate a decision or output. The output layer 506 includes one or more outputs each indicating a label, confidence factor, weight describing the inputs, and/or an output image. In some embodiments, however, outputs of the neural network model 204 are obtained from a hidden layer 504-1 through 504-$n$ in addition to, or in place of, output(s) from the output layer(s) 506.

In some embodiments, each layer has a discrete, recognizable function with respect to input data. For example, if n is equal to 3, a first layer analyzes the first dimension of the inputs, a second layer the second dimension, and the final layer the third dimension of the inputs. Dimensions may correspond to aspects considered strongly determinative, then those considered of intermediate importance, and finally those of less relevance.

In other embodiments, the layers are not clearly delineated in terms of the functionality they perform. For example, two or more of hidden layers 504-1 through 504-$n$ may share decisions relating to labeling, with no single layer making an independent decision as to labeling.

Figure 5B:
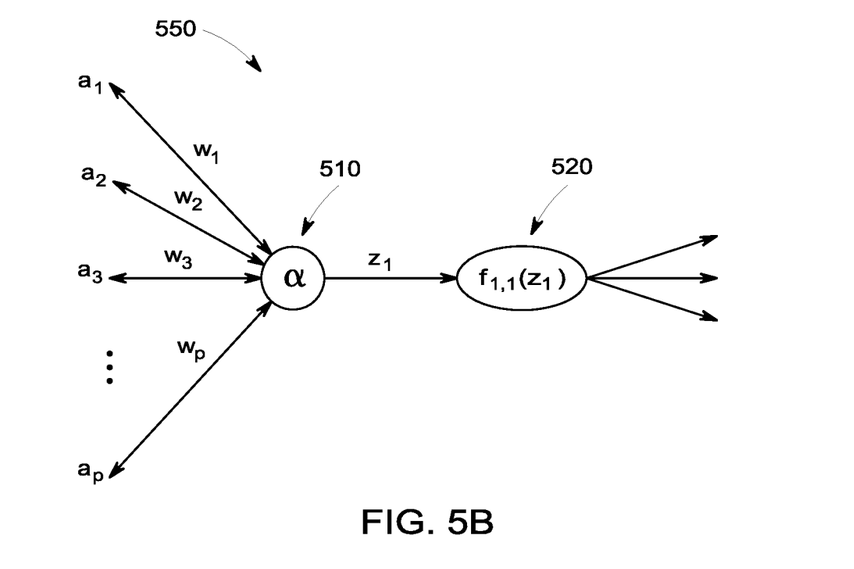
FIG. 5B is a schematic diagram of a neuron in the neural network model shown in FIG. 5A.

FIG. 5B depicts an example neuron 550 that corresponds to the neuron labeled as "1,1" in hidden layer 504-1 of FIG. 5A, according to one embodiment. Each of the inputs to the neuron 550 (e.g., the inputs in the input layer 502 in FIG. 5A) is weighted such that input $a_1$ through $a_p$ corresponds to weights $w_1$ through $w_p$ as determined during the training process of the neural network model 204.

In some embodiments, some inputs lack an explicit weight, or have a weight below a threshold. The weights are applied to a function α (labeled by a reference numeral 510), which may be a summation and may produce a value $z_1$ which is input to a function 520, labeled as $f_{1,1}(z_1)$. The function 520 is any suitable linear or non-linear function. As depicted in FIG. 5B, the function 520 produces multiple outputs, which may be provided to neuron(s) of a subsequent layer, or used as an output of the neural network model 204. For example, the outputs may correspond to index values of a list of labels, or may be calculated values used as inputs to subsequent functions.

It should be appreciated that the structure and function of the neural network model 204 and the neuron 550 depicted are for illustration purposes only, and that other suitable configurations exist. For example, the output of any given neuron may depend not only on values determined by past neurons, but also on future neurons.

The neural network model 204 may include a convolutional neural network (CNN), a deep learning neural network, a reinforced or reinforcement learning module or program, or a combined learning module or program that learns in two or more fields or areas of interest. Supervised and unsupervised machine learning techniques may be used. In supervised machine learning, a processing element may be provided with example inputs and their associated outputs, and may seek to discover a general rule that maps inputs to outputs, so that when subsequent novel inputs are provided the processing element may, based upon the discovered rule, accurately predict the correct output. The neural network model 204 may be trained using unsupervised machine learning programs. In unsupervised machine learning, the processing element may be required to find its own structure in unlabeled example inputs. Machine learning may involve identifying and recognizing patterns in existing data in order to facilitate making predictions for subsequent data. Models may be created based upon example inputs in order to make valid and reliable predictions for novel inputs.

Additionally or alternatively, the machine learning programs may be trained by inputting sample data sets or certain data into the programs, such as images, object statistics, and information. The machine learning programs may use deep learning algorithms that may be primarily focused on pattern recognition, and may be trained after processing multiple examples. The machine learning programs may include Bayesian Program Learning (BPL), voice recognition and synthesis, image or object recognition, optical character recognition, and/or natural language processing—either individually or in combination. The machine learning programs may also include natural language processing, semantic analysis, automatic reasoning, and/or machine learning.

Based upon these analyses, the neural network model 204 may learn how to identify characteristics and patterns that may then be applied to analyzing image data, model data, and/or other data. For example, the model 204 may learn to identify features in a series of data points.

Figure 6:
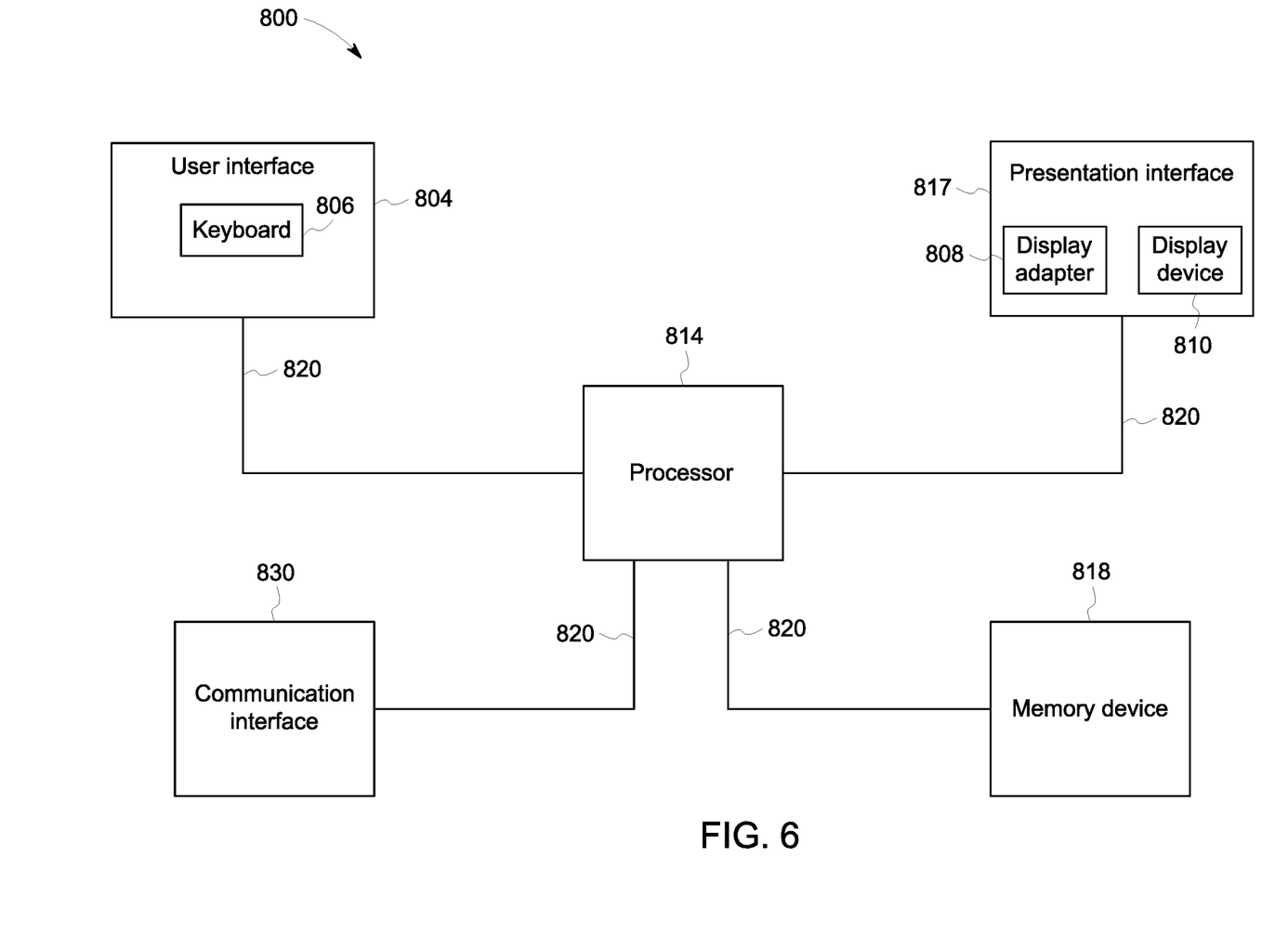
FIG. 6 is a block diagram of an exemplary computing device.

The workstation 12 and the MR image processing computing device 202, 203 described herein may be any suitable computing device 800 and software implemented therein. FIG. 6 is a block diagram of an exemplary computing device 800. In the exemplary embodiment, the computing device 800 includes a user interface 804 that receives at least one input from a user. The user interface 804 may include a keyboard 806 that enables the user to input pertinent information. The user interface 804 may also include, for example, a pointing device, a mouse, a stylus, a touch sensitive panel (e.g., a touch pad and a touch screen), a gyroscope, an accelerometer, a position detector, and/or an audio input interface (e.g., including a microphone).

Moreover, in the exemplary embodiment, computing device 800 includes a presentation interface 817 that presents information, such as input events and/or validation results, to the user. The presentation interface 817 may also include a display adapter 808 that is coupled to at least one display device 810. More specifically, in the exemplary embodiment, the display device 810 may be a visual display device, such as a cathode ray tube (CRT), a liquid crystal display (LCD), a light-emitting diode (LED) display, and/or an "electronic ink" display. Alternatively, the presentation interface 817 may include an audio output device (e.g., an audio adapter and/or a speaker) and/or a printer.

The computing device 800 also includes a processor 814 and a memory device 818. The processor 814 is coupled to the user interface 804, the presentation interface 817, and the memory device 818 via a system bus 820. In the exemplary embodiment, the processor 814 communicates with the user, such as by prompting the user via the presentation interface 817 and/or by receiving user inputs via the user interface 804. The term "processor" refers generally to any programmable system including systems and microcontrollers, reduced instruction set computers (RISC), complex instruction set computers (CISC), application specific integrated circuits (ASIC), programmable logic circuits (PLC), and any other circuit or processor capable of executing the functions described herein. The above examples are exemplary only, and thus are not intended to limit in any way the definition and/or meaning of the term "processor."

In the exemplary embodiment, the memory device 818 includes one or more devices that enable information, such as executable instructions and/or other data, to be stored and retrieved. Moreover, the memory device 818 includes one or more computer readable media, such as, without limitation, dynamic random access memory (DRAM), static random access memory (SRAM), a solid state disk, and/or a hard disk. In the exemplary embodiment, the memory device 818 stores, without limitation, application source code, application object code, configuration data, additional input events, application states, assertion statements, validation results, and/or any other type of data. The computing device 800, in the exemplary embodiment, may also include a communication interface 830 that is coupled to the processor 814 via the system bus 820. Moreover, the communication interface 830 is communicatively coupled to data acquisition devices.

In the exemplary embodiment, the processor 814 may be programmed by encoding an operation using one or more executable instructions and providing the executable instructions in the memory device 818. In the exemplary embodiment, the processor 814 is programmed to select a plurality of measurements that are received from data acquisition devices.

In operation, a computer executes computer-executable instructions embodied in one or more computer-executable components stored on one or more computer-readable media to implement aspects of the invention described and/or illustrated herein. The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

At least one technical effect of the systems and methods described herein includes (a) MR image processing of MR data having a higher number of dimensions using a neural network model having a lower number of dimensions to output processed MR images having the higher number of dimensions; and (b) training a neural network model with training data having a lower number of dimensions; (c) a neural network model having a plurality of neural networks being applied in parallel; and (d) a neural network model having a plurality of neural networks being applied in series.

Exemplary embodiments of systems and methods of MR image processing are described above in detail. The systems and methods are not limited to the specific embodiments described herein but, rather, components of the systems and/or operations of the methods may be utilized independently and separately from other components and/or operations described herein. Further, the described components and/or operations may also be defined in, or used in combination with, other systems, methods, and/or devices, and are not limited to practice with only the systems described herein.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A magnetic resonance (MR) image processing system, comprising an MR image processing computing device, the MR image processing computing device comprising at least one processor in communication with at least one memory device, and the at least one processor programmed to:
   execute a neural network model, wherein the neural network model includes a plurality of neural networks and is configured to receive crude MR data having a first number of dimensions as an input and configured to output processed MR images associated with the crude MR data, the processed MR images having the first number of dimensions;
   receive a pair of pristine data and corrupted data, wherein the pristine data and the corrupted data have a second number of dimensions that is lower than the first number of dimensions, and the corrupted data are the pristine data added with primitive features; and
   train the neural network model using the pair of the pristine data and the corrupted data by:
      inputting the corrupted data to the neural network model;
      setting the pristine data as target outputs of the neural network model;
      analyzing the corrupted data using the neural network model;
      comparing outputs of the neural network model with the target outputs; and
      adjusting the neural network model based on the comparison,
   wherein the trained neural network model is configured to change primitive features associated with the crude MR data.

2. The system of claim 1, wherein the primitive features are associated with undersampling along a dimension.

3. The system of claim 1, wherein the primitive features include artifacts.

4. The system of claim 1, wherein the primitive features include parameter maps.

5. The system of claim 1, wherein the pristine data are non-MR data.

6. A magnetic resonance (MR) image processing system, comprising an MR image processing computing device, the MR image processing computing device comprising at least one processor in communication with at least one memory device, and the at least one processor programmed to:
receive crude MR data having a first number of dimensions;
analyze the crude MR data using a neural network model, wherein the neural network model includes a plurality of neural networks and was trained with a pair of pristine data and corrupted data, the pristine data and the corrupted data having a second number of dimensions that is lower than the first number of dimensions, wherein the corrupted data are the pristine data added with primitive features, and the neural network model is configured to take the crude MR data as input and output processed MR images of the crude MR data, the processed MR images having the first number of dimensions;
derive the processed MR images of the crude MR data based on the analysis; and
output the processed MR images.

7. The system of claim 6, wherein the at least one processor is further programmed to:
analyze the crude MR data using the neural network model by:
applying the plurality of neural networks in parallel on the crude MR data, wherein each dimension of the crude MR data is analyzed by the plurality of neural networks at least twice; and
consolidating outputs of the plurality of neural networks; and
derive the processed MR images as the consolidated outputs.

8. The system of claim 7, wherein the at least one processor is further programmed to:
consolidate the outputs by averaging the outputs of the plurality of neural networks.

9. The system of claim 7, wherein the at least one processor is further programmed to:
consolidate the outputs by computing the consolidated outputs as weighted sums of the outputs of the plurality of neural networks.

10. The system of claim 7, wherein the at least one processor is further programmed to:
consolidate the outputs by an agent.

11. The system of claim 6, wherein the at least one processor is further programmed to:
analyze the crude MR data using the neural network model by:
applying the plurality of neural networks in series on the crude MR data; and
derive the processed MR images as an output of the last neural network applied in the neural network model.

12. The system of claim 6, wherein one of the plurality of neural networks has a different number of dimensions from another one of the plurality of neural networks.

13. The system of claim 6, wherein one of the plurality of neural networks is trained with different training data from another one of the plurality of neural networks.

14. The system of claim 6, wherein one of the plurality of neural networks is a different type of neural network from another one of the plurality of neural networks.

15. The system of claim 6, wherein the at least one processor is further programmed to repeat analyzing the crude MR data using the neural network model for a number of times.

16. The system of claim 6, wherein the crude MR data are in a hybrid space.

17. The system of claim 6, wherein the at least one processor is further programmed to:
enhance the crude MR data by analyzing the crude MR data using the neural network model, wherein primitive features associated with the processed MR images are reduced, compared to primitive features associated with the crude MR data.

18. The system of claim 6, wherein the crude MR data are acquired by undersampling along a dimension and the processed MR images are fully sampled along the dimension.

19. The system of claim 6, wherein the processed MR images are parameter maps of the crude MR data.

* * * * *

UNITED STATES PATENT AND TRADEMARK OFFICE
CERTIFICATE OF CORRECTION

| | | |
|---|---|---|
| PATENT NO. | : 12,118,720 B2 | Page 1 of 1 |
| APPLICATION NO. | : 17/644857 | |
| DATED | : October 15, 2024 | |
| INVENTOR(S) | : Robert Marc Lebel et al. | |

It is certified that error appears in the above-identified patent and that said Letters Patent is hereby corrected as shown below:

On the Title Page

In item (72), Line 4, please replace "Mckinnon" with -- McKinnon --.

Signed and Sealed this
Nineteenth Day of November, 2024

*Katherine Kelly Vidal*

Katherine Kelly Vidal
*Director of the United States Patent and Trademark Office*